(12) United States Patent
Oki et al.

(10) Patent No.: US 8,223,917 B2
(45) Date of Patent: Jul. 17, 2012

(54) METHOD OF QUANTITATIVE ANALYSIS OF HEXAVALENT CHROMIUM IN CHROMATE COATING AND METHOD FOR CONTROLLING HAZARDOUS ELEMENT IN ENCAPSULATING RESIN OF RESIN ENCAPSULATION SEMICONDUCTOR DEVICE

(75) Inventors: Mitsuhiro Oki, Yokohama (JP); Miyuki Takenaka, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 464 days.

(21) Appl. No.: 12/575,745

(22) Filed: Oct. 8, 2009

(65) Prior Publication Data
US 2010/0091944 A1   Apr. 15, 2010

Related U.S. Application Data

(63) Continuation-in-part of application No. 11/511,331, filed on Aug. 29, 2006, now abandoned.

(30) Foreign Application Priority Data

Sep. 1, 2005 (JP) .................................. 2005-253015

(51) Int. Cl.
*G01N 23/223* (2006.01)
(52) U.S. Cl. ......................................................... 378/45
(58) Field of Classification Search .................... 378/44, 378/45, 46, 49, 50
See application file for complete search history.

(56) References Cited

U.S. PATENT DOCUMENTS

| | | | | |
|---|---|---|---|---|
| 5,570,406 | A | * | 10/1996 | Komatani ........................ 378/44 |
| 6,118,844 | A | * | 9/2000 | Fischer ............................ 378/48 |
| 6,808,931 | B1 | | 10/2004 | Wang et al. |
| 2003/0058990 | A1 | * | 3/2003 | Kaiser et al. .................... 378/45 |
| 2004/0086438 | A1 | | 5/2004 | Sreeram et al. |
| 2007/0248211 | A1 | * | 10/2007 | Tani et al. ....................... 378/45 |

FOREIGN PATENT DOCUMENTS

| | | |
|---|---|---|
| JP | 5-164710 | 6/1993 |
| JP | 2004-325321 | 11/2004 |
| JP | 2007-3331 | 1/2007 |
| JP | 2007-17306 | 1/2007 |

OTHER PUBLICATIONS

"Alkaline Digestion for Hexavalent Chromium", Method 3060A, Dec. 1996, pp. 3060A1-3060A15.
"Chromate Converstion Coatings on Zinc, Cadmium, Aluminium-Zinc Alloys and Zinc-Aluminium Alloys-Test methods", International Standard, ISO 3613, Jun. 15, 2000, 10 Pages.
Lindsay F. G. Williams, Determination of the Chromate Content of Chromate Conversion Films on Zinc, Analytica Chimica Acta, vol. 94, pp. 199-200, 1977.

* cited by examiner

*Primary Examiner* — Irakli Kiknadze
(74) *Attorney, Agent, or Firm* — Oblon, Spivak, McClelland, Maier & Neustadt, L.L.P.

(57) ABSTRACT

A method for controlling a hazardous element in an encapsulating resin of a resin encapsulation semiconductor device includes subjecting the device to qualitative analysis with a fluorescent X-ray analyzer to judge whether the hazardous element is contained in the encapsulating resin, aligning a plurality of devices with each of upper and lower surfaces of the devices brought into a plane, setting the surfaces of the devices to cover a full X-ray irradiation plane and subjecting the devices to quantitative analysis with the fluorescent X-ray analyzer to obtain an analytical value of the hazardous element in the encapsulating resin for upper and lower surfaces of the devices, and judging whether the analytical value of the hazardous element which is less influenced by a coexistent element of the analytical values for the upper and lower surfaces of the devices exceeds a threshold value.

5 Claims, 6 Drawing Sheets

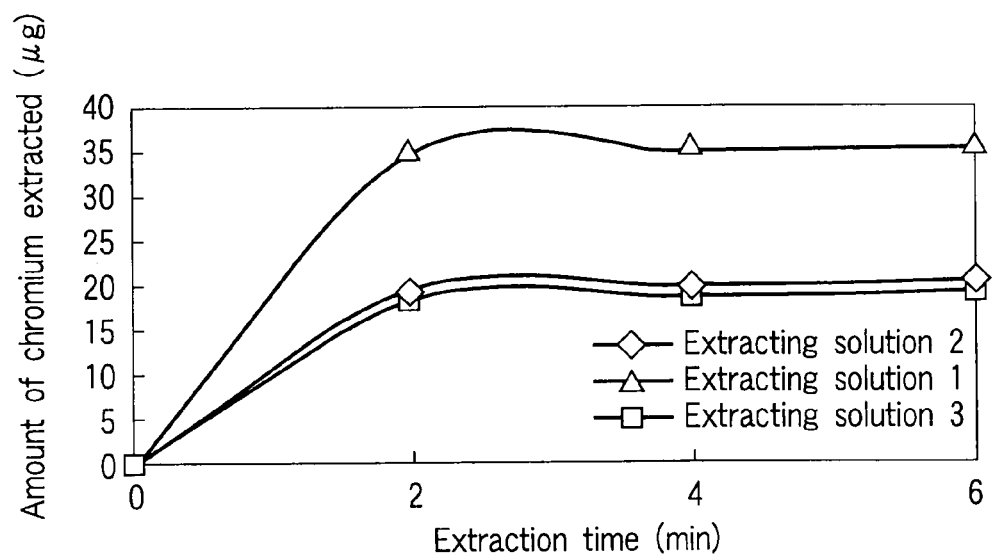
F I G. 1
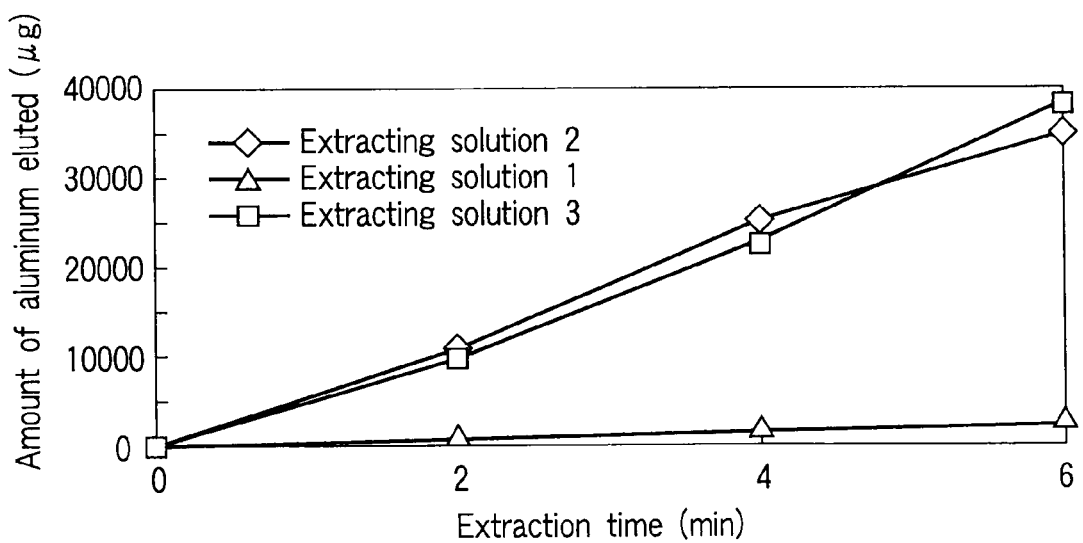
F I G. 2

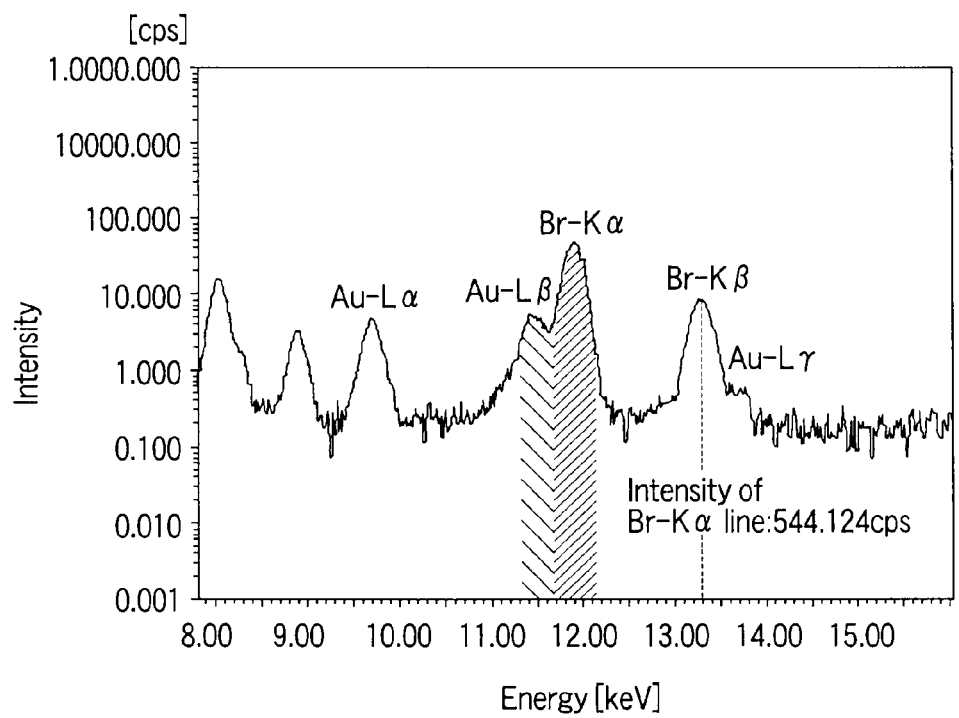
F I G. 6A
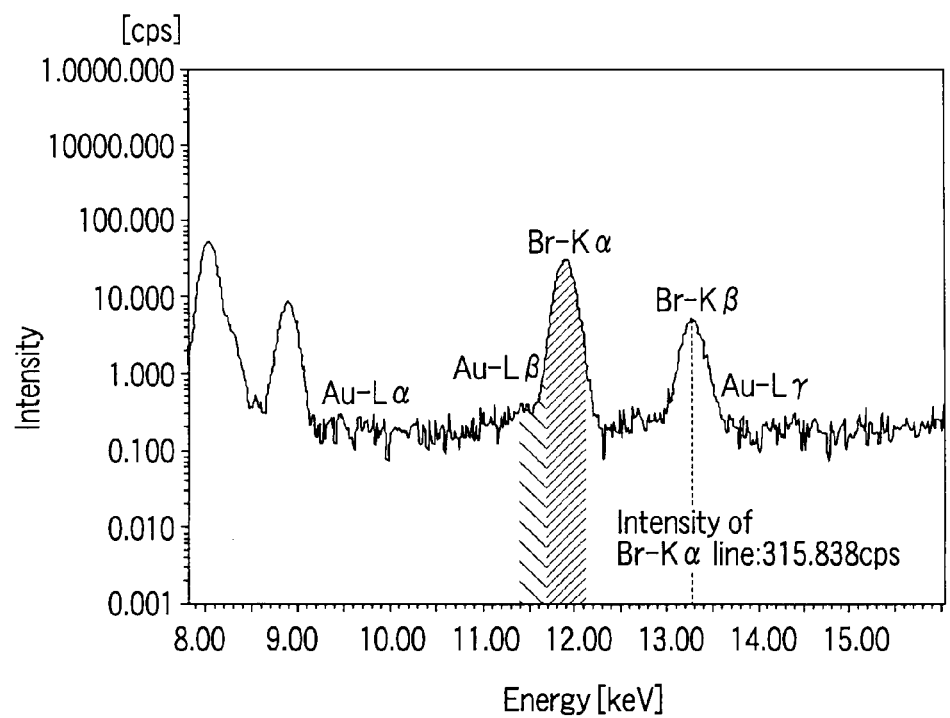
F I G. 6B

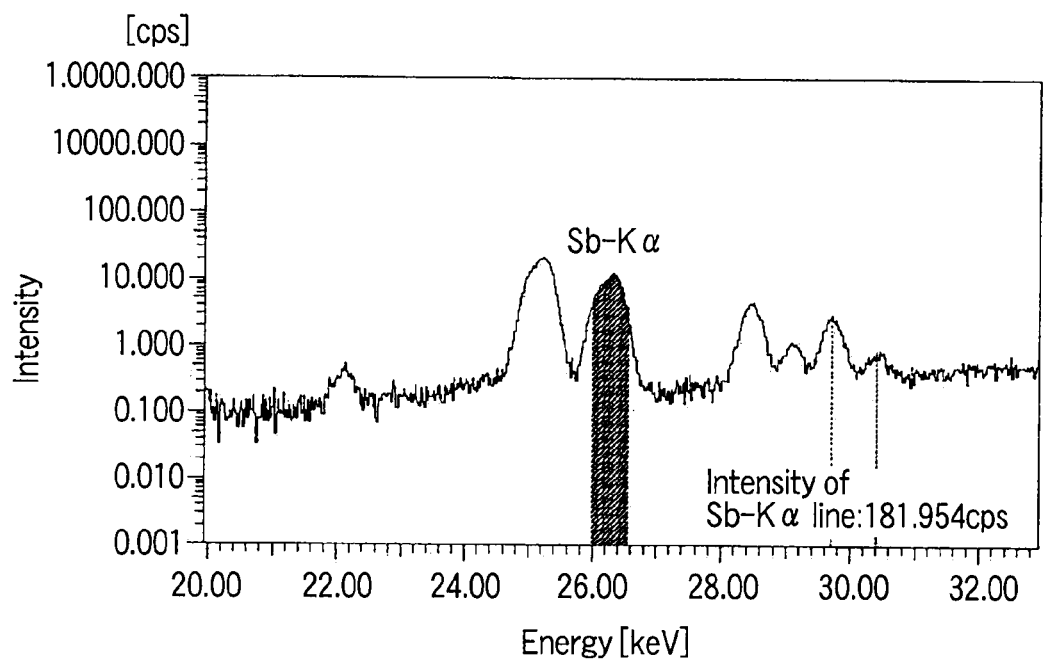
F I G. 7A
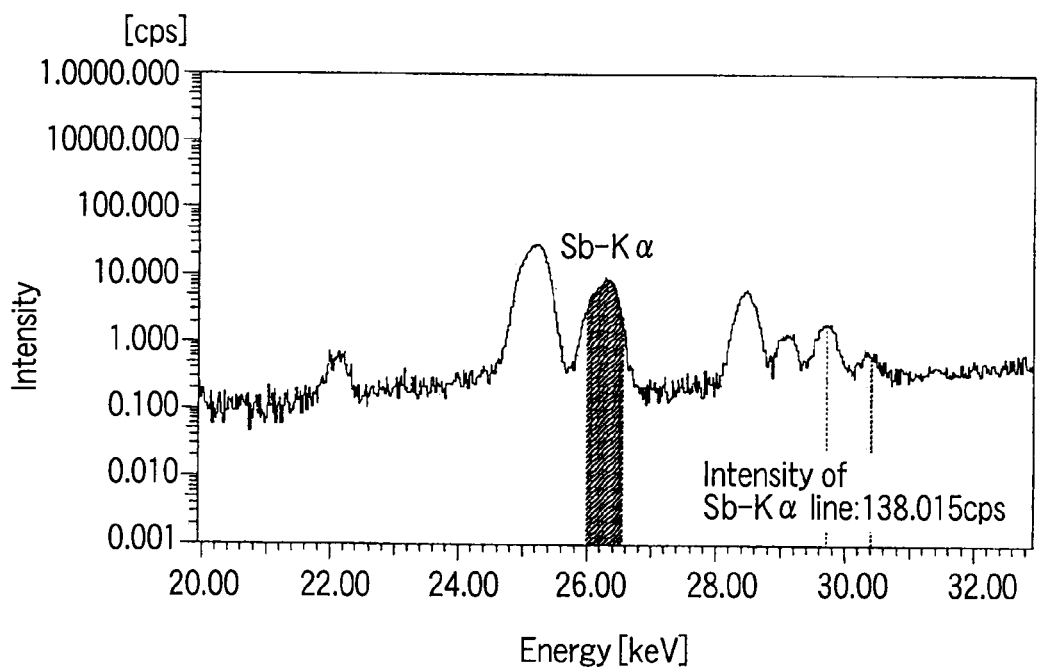
F I G. 7B

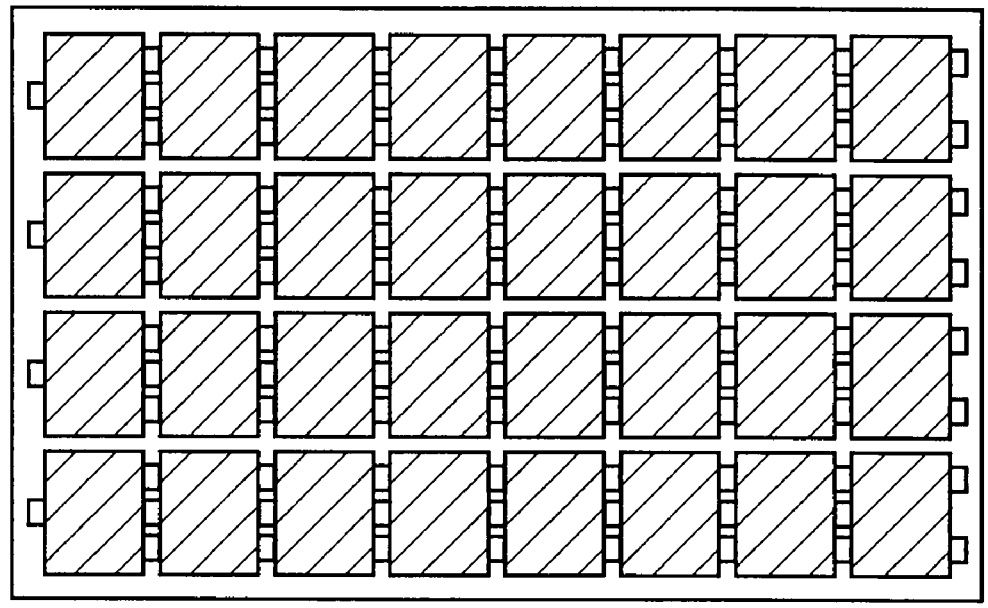
F I G. 8A
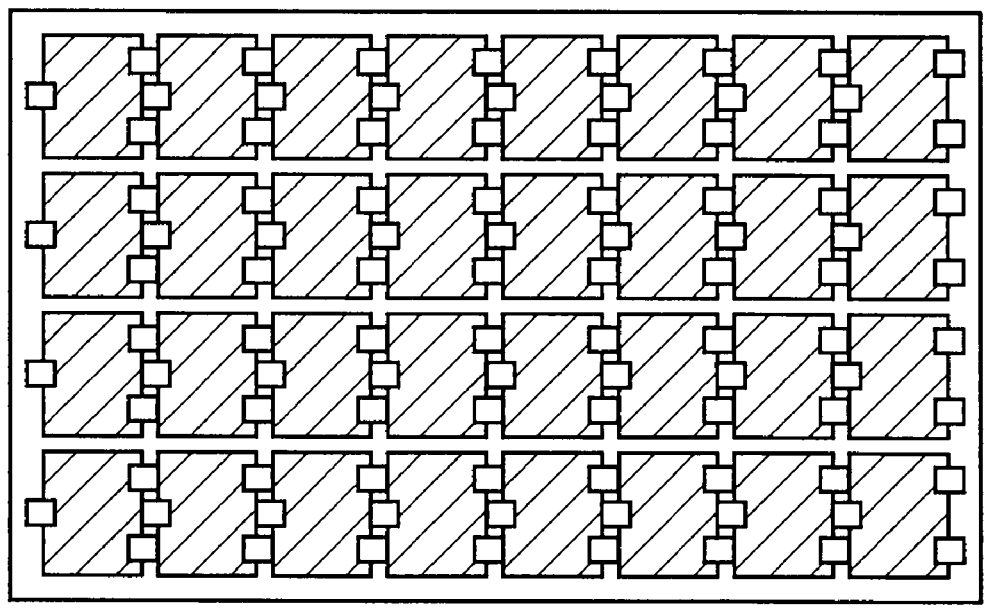
F I G. 8B

METHOD OF QUANTITATIVE ANALYSIS OF HEXAVALENT CHROMIUM IN CHROMATE COATING AND METHOD FOR CONTROLLING HAZARDOUS ELEMENT IN ENCAPSULATING RESIN OF RESIN ENCAPSULATION SEMICONDUCTOR DEVICE

CROSS-REFERENCE TO RELATED APPLICATIONS

This is a Continuation-in-Part application of U.S. patent application Ser. No. 11/511,331, filed Aug. 29, 2006, the entire contents of which are incorporated herein by reference.

This application is based upon and claims the benefit of priority from prior Japanese Patent Application No. 2005-253015, filed Sep. 1, 2005, the entire contents of which are incorporated herein by reference.

BACKGROUND OF THE INVENTION

1. Field of the Invention

The present invention relates to a method of quantitative analysis of hexavalent chromium in a coating for a metal substrate such as a chromate coating used in household electronic appliances and automobiles. The present invention also relates to a method for controlling a hazardous element in an encapsulating resin of a resin encapsulation semiconductor device with a fluorescent X-ray analyzer.

2. Description of the Related Art

In Europe, it is required to restrict the use of lead, mercury, cadmium, PBB, PBDE, and hexavalent chromium in principle in accordance with the Restriction of Hazardous Substances Directive (ROHS) which takes effect on Jul. 1, 2006. In order to comply with the directive, it is desired to develop analytical methods capable of conveniently assaying these substances.

It is known that X-ray photoelectron spectroscopy can be used as an analytical method for directly assaying hexavalent chromium content in a chromate coating (see Jpn. Pat. Appln. KOKAI No. H05-164710). Since this method assays only the surface of the coating, however, there are problems that the analytical value does not represent the value for the entire sample and that it is hard to separate peaks of trivalent chromium and hexavalent chromium.

ISO 3613 defines an analytical method for determining hexavalent chromium eluted from a chromate coating using boiling water. This method assays only hexavalent chromium eluted by the boiling water, and cannot determine total hexavalent chromium content present in the chromate coating.

An analytical method using sodium hydroxide solution as an extracting solution is known in "Method 3060" defined by the United States Environmental Protection Agency (EPA). When a chromate coating on a substrate of an amphoteric metal such as aluminum is assayed using the extracting solution, the aluminum substrate is eluted prior to the chromate coating accompanied by hydrogen gas generation and reduction of hexavalent chromium to trivalent chromium, making it difficult to perform highly accurate quantitative analysis of hexavalent chromium.

Further, as an analytical method of efficiently extracting hexavalent chromium in a chromate coating on a metal substrate in a short time, a method is known in which the chromate coating is cracked and then the coating is immersed in an extracting solution to extract hexavalent chromium so as to be analyzed (see Jpn. Pat. Appln. KOKAI No. 2004-325321). Since this method requires to applying thermal shock or mechanical shock to the substrate in order to cause cracks, however, there is a possibility that the substrate itself may be broken. Thus, this method cannot be generally used for analyzing hexavalent chromium.

In addition, according to the RoHS directive, it is required to determine that particular hazardous substances are not contained in an electronic material. In compliance with the RoHS directive, it is expected to develop an analytical method capable of measuring hazardous elements such as Br, Sb, As, Bi and Pb easily and precisely and a method for controlling the hazardous elements precisely using the analytical method.

In order to non-destructively analyze hazardous elements in an encapsulating resin of a resin encapsulation semiconductor device, use of a fluorescent X-ray analyzer is easy and effective. The fluorescent X-ray analysis generally employs a fundamental parameter (FP) method for a metal sample and a calibration curve method for a resin sample. In order to prepare the calibration curve, standard resin samples are used to which a known quantity of element to be analyzed is added. The standard resin samples having a matrix resin such as polyethylene, ABS resin and vinyl chloride resin are commercially available.

Since the encapsulating resin is compressed in molding, it has a higher density than the standard resin samples. In addition, the encapsulating resin contains filler such as silica for enhancing strength. Thus, a primary X-ray is hard to penetrate into the encapsulating resin, which tends to bring about a lower analytical value of a fluorescent X-ray. Further, when the encapsulating resin of the resin encapsulation semiconductor device is analyzed with a fluorescent X-ray analyzer, there is a possibility to detect a fluorescent X-ray of constituent elements of a lead frame, semiconductor chip and wire, which may be a cause of an error for a fluorescent X-ray of some hazardous element to be detected.

Conventionally, there is proposed a method for judging whether a sample such as polystyrene contains lead (Pb) by fluorescent X-ray analysis. See JP-A 2007-3331 (KOKAI). The method comprises applying an X-ray to a sample, preparing a fluorescent X-ray spectrum, and judging that the sample contains Pb when the spectrum has peaks at all energy positions corresponding to Pb. The method aims at analyzing Pb precisely by avoiding influence of As or Br having a peak overlapping the peak of Pb. However, the method cannot solve the problem of precision due to the lower analytical value for an encapsulating resin of a resin encapsulation semiconductor device which is compressed and has a high density as well as contains filler.

Also, there is known a method for judging a material containing a particular substance in an object to be measured in which materials are formed in layers by fluorescent X-ray analysis. See JP-A 2007-17306 (KOKAI). This publication discloses a sample of Fe on which Zn plating and Cr plating are deposited as the object of layered structure and particular substances such as Cd, Pb, Hg, Br, Cr, Au, Ag, Pt and Pd. The method comprising applying an X-ray to a sample at a controlled depth by varying X-ray irradiation conditions, detecting a fluorescent X-ray emitted from the sample, and judging the material in the layered structure in which the particular substance is contained based on synchronous detention of the material and particular substance. The method is effective for a sample having a relatively simple layered structure and capable of providing sufficient fluorescent X-ray intensity. However, the method cannot solve the problem of precision due to the lower analytical value for an encapsulating resin of a resin encapsulation semiconductor device which is compressed and has a high density as well as contains filler. In addition, the method is not suited for analyzing an encapsulating resin of a resin encapsulation semiconductor device in which a lead frame, chip and wire are arranged into a complicated structure in a matrix resin.

BRIEF SUMMARY OF THE INVENTION

According to an aspect of the present invention, there is provided a method of quantitative analysis of hexavalent chromium in a chromate coating, comprising: immersing a substrate on which a chromate coating is formed in an aqueous solution containing lithium hydroxide to extract hexavalent chromium; and performing quantitative analysis of extracted hexavalent chromium.

According to another aspect of the present invention, there is provided a method for controlling a hazardous element in an encapsulating resin of a resin encapsulation semiconductor device, comprising: subjecting the device to qualitative analysis with a fluorescent X-ray analyzer to judge whether the hazardous element is contained in the encapsulating resin; aligning a plurality of devices with each of upper and lower surfaces of the devices brought into a plane; setting the surfaces of the devices to cover a full X-ray irradiation plane and subjecting the devices to quantitative analysis with the fluorescent X-ray analyzer to obtain an analytical value of the hazardous element in the encapsulating resin for upper and lower surfaces of the devices; and judging whether the analytical value of the hazardous element which is less influenced by a coexistent element of the analytical values for the upper and lower surfaces of the devices exceeds a threshold value.

BRIEF DESCRIPTION OF THE SEVERAL VIEWS OF THE DRAWING

FIG. 1 is a graph showing a relationship between an extraction time and an amount of extracted chromium when an aluminum substrate having a chromate coating is immersed in different extracting solutions;

FIG. 2 is a graph showing a relationship between an extraction time and an amount of eluded aluminum when an aluminum substrate having a chromate coating is immersed in different extracting solutions;

FIGS. 6A and 6B are fluorescent X-ray spectrums showing analysis of Br in Example 1;

FIGS. 7A and 7B are fluorescent X-ray spectrums showing analysis of Sb in Example 2; and FIGS. 8A and 8B are plan views showing upper and lower surfaces of aligned resin encapsulation semiconductor devices.

DETAILED DESCRIPTION OF THE INVENTION

Figure 3:
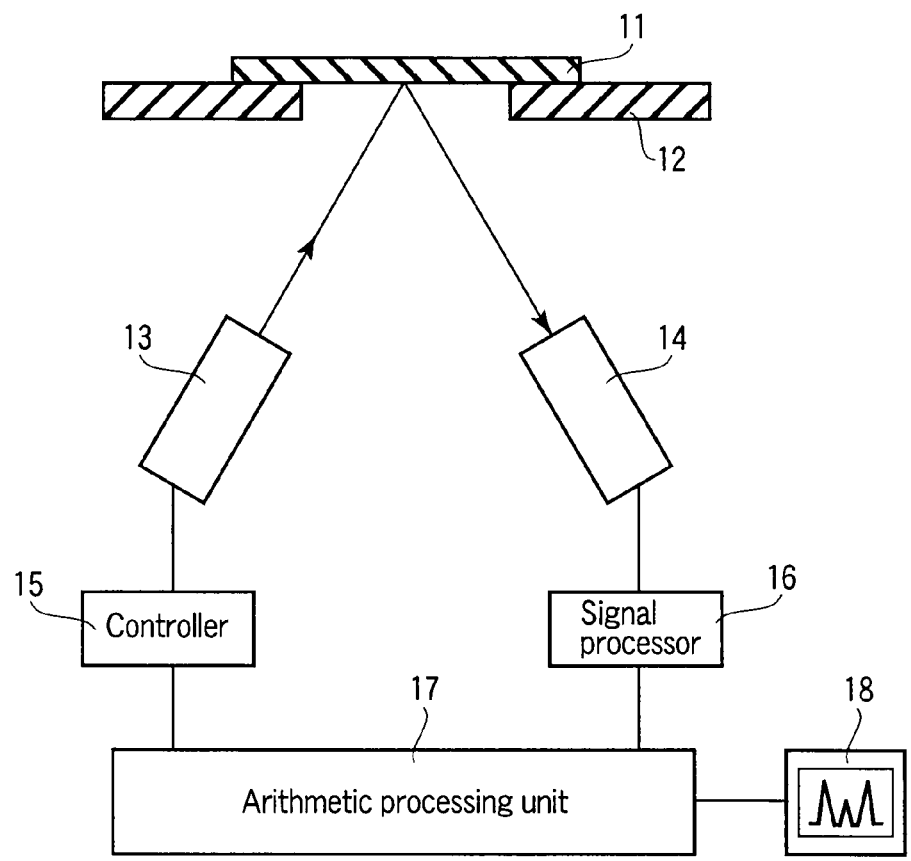
FIG. 3 is a schematic view of an energy-dispersive fluorescent X-ray spectrometer.

Embodiments of the present invention will be described below.

Chromating is carried out to improve corrosion resistance and coating performance of a metal substrate. The chromating is generally performed by immersing a metal substrate liable to be corroded in a chromic acid solution to form a chromate coating. The chromate coating includes those types called bright chromate, colored chromate, black chromate, and green chromate depending on a thickness, chromium content, other element content, and so forth. The present invention can be applied to any type of chromate.

The chromating method includes reactive chromating, application chromating, and electrolytic chromating. The chromating method is not particularly limited, and the present invention can be applied to a coating formed by any type of chromating.

A metal substrate used is not particularly limited. The metal substrate includes, for example, a zinc-plated steel substrate for improving corrosion protection, the surface of which is chromated. The metal substrate also includes an aluminum substrate liable to be corroded, the surface of which is chromated.

According to embodiments of the present invention, an aqueous solution containing lithium hydroxide is used as an extracting solution. If an extracting solution containing sodium hydroxide is used and the extracting solution is applied to an aluminum substrate, the sodium hydroxide corrodes the aluminum substrate, making it impossible to expect an accurate analytical result. In contrast, the aqueous solution containing lithium hydroxide does not corrode the aluminum substrate. Thus, the method according to embodiments of the present invention can be applied to any metal substrate.

In an embodiment of the present invention, a concentration of the lithium hydroxide in the extracting solution is preferably in a range of 0.8 to 1.3 wt %, and more preferably in a range of 0.9 to 1.1 wt %. If the concentration of the lithium hydroxide in the extracting solution is less than 0.8 wt %, the reaction of the lithium hydroxide with the chromate coating proceeds slowly, leading to disadvantageously long extraction time. If the concentration of the lithium hydroxide in the extracting solution exceeds 1.3 wt %, the lithium hydroxide reacts with the chromate coating intensively, and thus there is a disadvantageous possibility of reducing the hexavalent chromium.

Incidentally, it is preferable in the embodiments of the present invention to use lithium hydroxide with purity of reagent grade. However, the lithium hydroxide may contain another component such as potassium hydroxide as long as the component does not exert such an adverse effect of corroding the substrate or reducing haxavalent chromium.

It is preferable to set the temperature of the extracting solution to a range of 60 to 90° C. If the temperature of the extracting solution is lower than 60° C., the reaction of the lithium hydroxide with the chromate coating proceeds slowly, leading to disadvantageously long extraction time. If the temperature of the extracting solution exceeds 90° C., the lithium hydroxide reacts with the chromate coating intensively, and thus there is a disadvantageous possibility to reduce the hexavalent chromium.

The thus extracted hexavalent chromium can be assayed by general, high-precision quantitative analysis such as spectrophotometry using diphenylcarbazide.

Nest, a method for controlling a hazardous element in an encapsulating resin of a resin encapsulation semiconductor device will be described.

[Fluorescent X-Ray Spectrometer]

The fluorescent X-ray spectrometer used for elemental microanalysis includes a wavelength-dispersive fluorescent X-ray spectrometer and energy-dispersive fluorescent X-ray spectrometer. In the present invention, either type of fluorescent X-ray spectrometer may be used. However, it is preferable to use the energy-dispersive fluorescent X-ray spectrometer because it has a simple detector and a simple equipment configuration. FIG. 3 shows a schematic view of an energy-dispersive fluorescent X-ray spectrometer. As shown in FIG. 3, a sample 11 is mounted on a sample holder 12 and the sample 11 is irradiated with a primary X-ray generated from an X-ray generator 13 such as an X-ray tube. A fluorescent X-ray corresponding to an element contained in the sample is emitted from the sample 11 irradiated with the primary X-ray. The fluorescent X-ray intensity is detected with a detector such as a semiconductor detector 14. The X-ray generator 13 is controlled with a controller 15. The signals from the semiconductor detector 14 are processed with a signal processor 16 and then made into a spectrum with an arithmetic processing unit 17.

[Resin Encapsulation Semiconductor Device]

(Structure of Resin Encapsulation Semiconductor Device)

Figure 4:
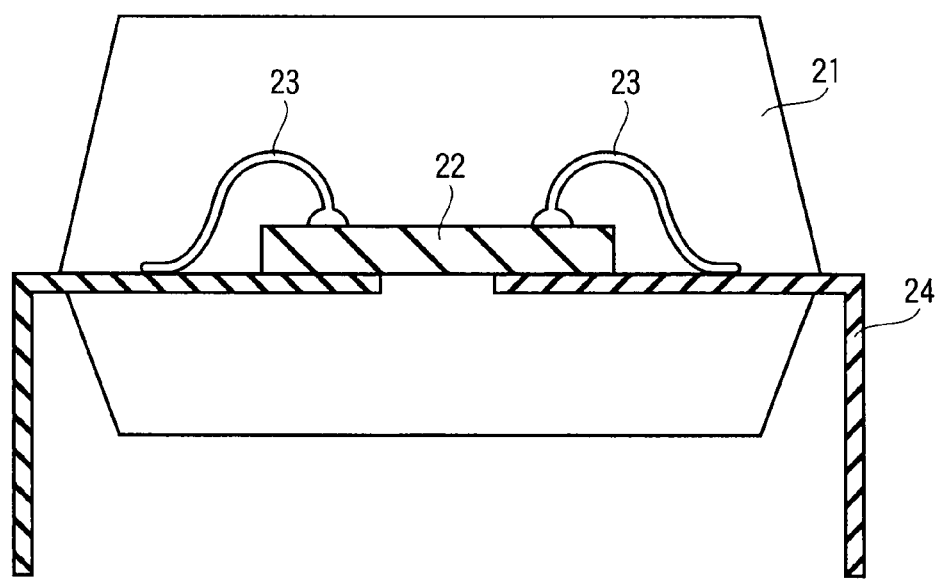
FIG. 4 is a cross-sectional view of a resin encapsulation semiconductor device.

FIG. 4 shows a cross-sectional view of a resin encapsulation semiconductor device. As shown in FIG. 4, a semiconductor chip 22 is mounted on a pad, and Au wires 23 electrically connect between contacts on the semiconductor chip 22 and a lead frame 24. The assembly comprising the semiconductor chip 22, lead frame 24 and Au wires 23 is encapsulated with an encapsulating resin 21. The encapsulating resin 21 serves to protect the semiconductor chip 22 from moisture and contaminants.

(Materials for Encapsulating Resin)

The encapsulating resin suitable for a semiconductor device comprises epoxy resin, filler and a curing agent.

The epoxy resin is not particularly limited as long as it has two or more epoxy groups in one molecular. Examples of the epoxy resin include biphenyl epoxy resin, phenol-novolak epoxy resin, cresol-novolak epoxy resin, naphthol-novolak epoxy resin, bisphenol-A epoxy resin, glycidyl ester epoxy resin, glycidyl amine epoxy resin, and alicyclic epoxy resin.

Examples of the filler include quartz glass, crystalline silica, fused silica, glass, alumina, calcium silicate, barium sulfate, silicon nitride, aluminum nitride, aluminum oxide, magnesium oxide, mica and metal. The amount of the filler is in a range of 70 to 90% by weight.

Examples of the curing agent include phenol-novolak resin, cresol-novolak resin, phenol-aralkyl resin, allylphenol-novolak resin, naphthol-novolak resin, biphenyl-novolak resin, and a tris(hydroxyphenyl)alkane compound.

The method according to embodiments is preferably applied to a resin encapsulation semiconductor device of which component comprises a coexistent element of at least one element selected from the group consisting of Au, Si, Cu, Fe, Ni, Sn, Bi, Pb, and Ag. This is because such a coexistent element has high probability of hindering the analysis of the hazardous element with a fluorescent X-ray spectrometer and reducing analytical precision.

[Analytical Method]

Figure 5:
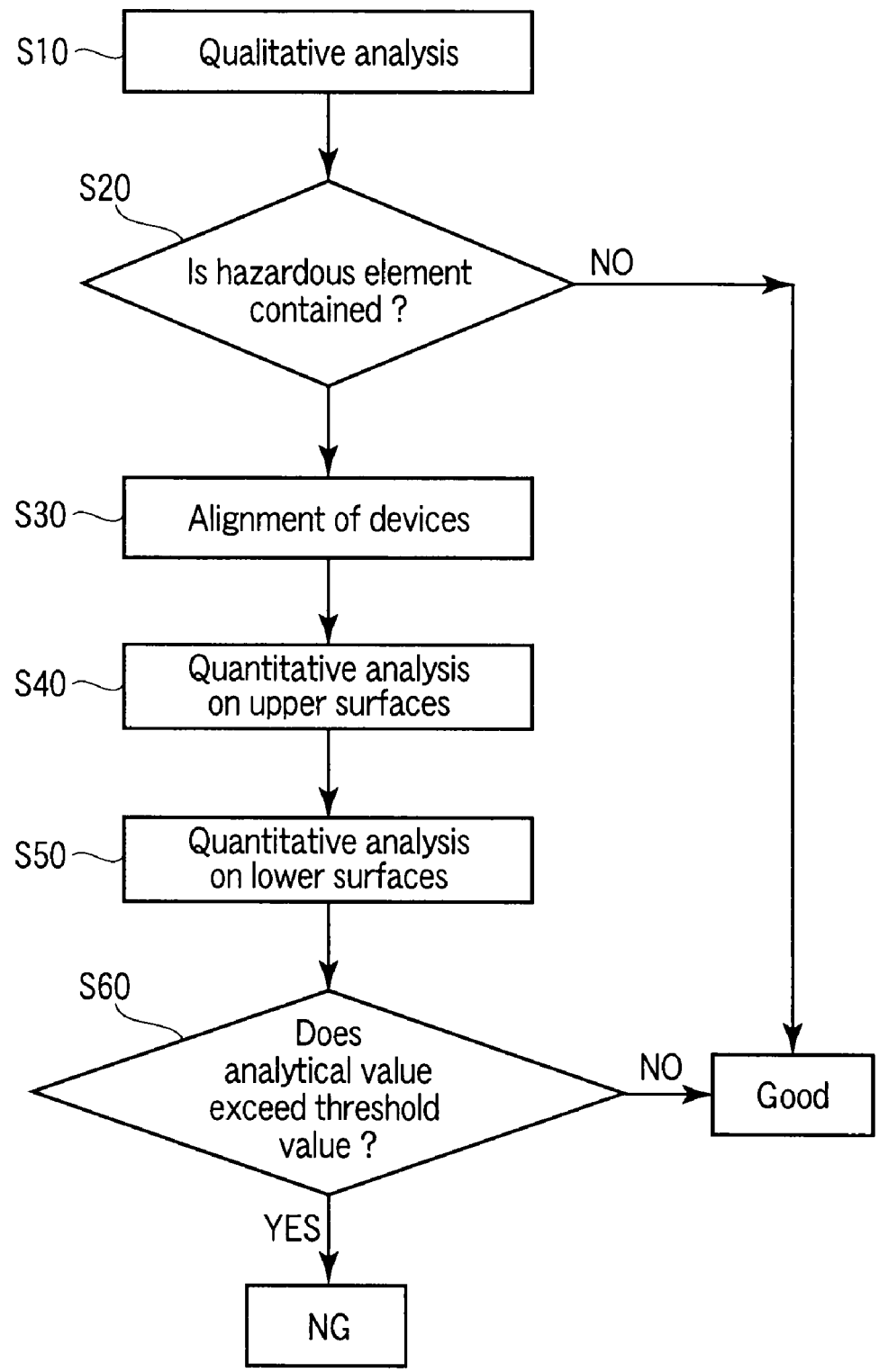
FIG. 5 is a flowchart showing a method according to an embodiment.

FIG. 5 shows a flowchart of the analytical method according to embodiments.

(S10 and S20: Qualitative Analysis and Judgment)

A resin encapsulation semiconductor device as a sample to be analyzed is prepared. Since fluorescent X-ray intensity emitted from the sample is weak in the fluorescent X-ray analysis of the resin encapsulation semiconductor device as described above, a plurality of resin encapsulation semiconductor devices are prepared when a device of a small size is to be analyzed. The qualitative analysis step S10 is performed for the purpose of judging whether the hazardous element is contained in the encapsulating resin. When it is judged that the hazardous element is not contained in the encapsulating resin in the judgment step S20, resin encapsulation semiconductor device is judged as a good product without performing the steps of S30 and later.

(S30: Device Alignment Step)

When it is judged that the hazardous element is contained in the encapsulating resin in the former step, a plurality of resin encapsulation semiconductor devices are aligned with each of upper and lower surfaces of the devices brought into a plane. FIG. 8A shows the upper surfaces of the aligned devices and FIG. 8B shows the lower surfaces of the aligned devices. As shown in FIGS. 8A and 8B, it is preferable that the devices are closely aligned without forming a gap between the devices. In general, the size of the X-ray irradiation plane of a fluorescent X-ray analyzer is approximately 10 mm in diameter. The devices are set such that the upper or lower surfaces of the devices cover the full X-ray irradiation plane. The reason why the devices are aligned with each of upper and lower surfaces of the devices brought into a plane is as follows.

In fluorescent X-ray analysis, a primary X-ray applied to a sample excites constituent elements of the sample by which a fluorescent X-ray is emitted. Since the applied primary X-ray is absorbed by the constituent elements from the surface of the sample to the thickness direction, the primary X-ray does not completely penetrate the sample. Therefore, the observed fluorescent X-ray spectrum is strongly influenced by the constituent elements of the sample which exist near the X-ray irradiation plane.

As shown in FIG. 4, the typical resin encapsulation semiconductor device has different components on the upper surface side and on the lower surface side. When the primary X-ray is applied to the upper surface of the sample, the fluorescent X-ray spectrum is mainly influenced by the encapsulating resin and Au wires. When the primary X-ray is applied to the lower surface of the sample, the fluorescent X-ray spectrum is mainly influenced by the encapsulating resin and lead frame.

When the energy value of the fluorescent X-ray peak of the hazardous element to be analyzed is close to the energy value of the fluorescent X-ray peak of the coexistent element contained in the components, the analytical value of the hazardous element has an error due to influence of the coexistent element. Therefore, the devices are aligned with each of upper and lower surfaces of the devices brought into a plane so that the analysis can be performed on the surfaces where the influence of the coexistent element is small.

(S40: Analysis on Upper Surfaces)

In this step, a primary X-ray is applied to the upper surfaces of the aligned devices to detect a fluorescent X-ray. Obtained results are made into a spectrum and recorded by the signal processor 16 and the arithmetic processing unit 17.

(S50: Analysis on Lower Surfaces)

In this step, a primary X-ray is applied to the lower surfaces of the aligned devices to detect a fluorescent X-ray. Obtained results are also made into a spectrum and recorded by the signal processor 16 and the arithmetic processing unit 17.

(S60: Judgment by Comparison with Threshold Value)

In this step, whether the analytical value of the hazardous element exceeds a threshold value based on the analysis results on the upper and lower surfaces.

First, two spectrums obtained in the steps S40 and S50 are compared with each other and a spectrum less influenced by coexistent elements is selected and employed as the quantitative analysis data.

Next, employed spectrum data is subjected to background correction. The background correction is described below. When a primary X-ray is applied to the sample, a part of the primary X-ray penetrated into the sample is reflected and emitted as a scattered X-ray. Thus, if a region (area or thickness) on which the primary X-ray is applied is changed, this change influences the fluorescent X-ray intensity. In order to cancel the influence due to the change in the region on which the primary X-ray is applied, the background correction is carried out. More specifically, the fluorescent X-ray intensity of the hazardous element is divided by the scattered X-ray intensity for normalization. The background correction reduces analytical error and improves analytical precision.

The concentration of the hazardous element is calculated from the normalized fluorescent X-ray intensity using a calibration curve obtained from standard samples.

The calibration curve is prepared by correlating the fluorescent X-ray intensity and the concentration of the hazardous element using commercially available, usual standard samples containing a known concentration of hazardous element. Usual standard samples have a matrix resin such as polyethylene, ABS resin and vinyl chloride resin as described above. However, these resins are different from the encapsulating resin of the practical resin encapsulation semiconductor device. In the present invention, it is preferable to use standard samples having a matrix resin comprising epoxy resin used as a general encapsulating resin.

The concentration of the hazardous element contained in the devices is determined as described above. The concentration is determined for every hazardous element.

The obtained analytical value of the hazardous element is compared with a threshold value that is an acceptable value as a good product to judge whether the analytical value exceeds the threshold value. The product judged as an inferior product is excluded from shipment, for example, under manufacturing control.

Also, when the inferior product is found by judgment, a process in which the hazardous element of a higher concentration exceeding the standard is identified and improved for process control.

The method of the present invention is suitable to quantitative analysis for Br and Sb among the hazardous elements prescribed in RoHS. Br has a peak the energy position of which is close to that of Au present in the resin encapsulation semiconductor device, and therefore it likely to have an analytical error. Sb tends to have a low analytical value in a sample having a high density.

Other Embodiment

In the above embodiments, the fluorescent X-ray analysis is performed in a state that a plurality of resin encapsulation semiconductor devices are aligned. This is because the fluorescent X-ray intensity becomes higher and the analytical precision can be improved as the X-ray irradiation area becomes large, a plurality of devices are aligned on the X-ray irradiation plane. In contrast, a resin encapsulation semiconductor device of power semiconductor, for example, has a large size and only one device can sufficiently cover the X-ray irradiation plane. In analyzing such a large-sized resin encapsulation semiconductor device, only one device mounted on the sample holder and there is no need to align a plurality of devices.

EXAMPLES

The present invention will be described in more detail based on examples.

Example 1

(Substrate)
An aluminum plate (A5052), 20 mm×20 mm×0.5 mm in thickness, having a chromate coating with a thickness of 250 nm was used as a substrate.

(Extraction)
The sample was placed in a 30-mL glass beaker to which an extracting solution was added so as to immerse the sample in the extracting solution. As the extracting solution, a 1 wt % aqueous solution of lithium hydroxide (extracting solution 1, Example), a 1 wt % aqueous solution of sodium hydroxide (extracting solution 2, Comparative Example), or a mixed aqueous solution of sodium hydroxide and sodium carbonate (extracting solution 3, Comparative Example) was used. The beaker was placed on a hot plate. The extracting solution was heated over a predetermined period of time to extract hexavalent chromium in the chromate coating.

(Quantitative Analysis)
The resultant hexavalent chromium extract was allowed to natural cooling, and then transferred to a 50-mL volumetric flask to which 2 mL of 25% sulfuric acid was added to make the extract acidic. Then, quantitative analysis of hexavalent chromium was performed by the official method of spectrophotometry using diphenylcarbazide. FIG. 1 shows the results. FIG. 1 is a graph showing a relationship between an extraction time and an amount of extracted chromium for different extracting solutions.

An amount of aluminum eluted from the substrate was also measured. FIG. 2 shows the results. FIG. 2 is a graph showing a relationship between an extraction time and an amount of eluded aluminum for different extracting solutions.

As is shown in FIG. 1, the amounts of extracted chromium are: 35 μg for the 1 wt % aqueous solution of lithium hydroxide (extracting solution 1), 20 μg for the 1 wt % aqueous solution of sodium hydroxide (extracting solution 2), and 19 μg for the mixed aqueous solution of sodium hydroxide and sodium carbonate (extracting solution 3). It is found that, when the 1 wt % aqueous solution of sodium hydroxide (extracting solution 2) or the mixed aqueous solution of sodium hydroxide and sodium carbonate (extracting solution 3) is used, 40% of hexavalent chromium is reduced compared with that extracted when the 1 wt % aqueous solution of lithium hydroxide (extracting solution 1) is used.

It is found that, when the 1 wt % aqueous solution of lithium hydroxide (extracting solution 1) is used, the amount of aluminum eluted from the substrate is very small compared with that eluted when the 1 wt % aqueous solution of sodium hydroxide (extracting solution 2) or the mixed aqueous solution of sodium hydroxide and sodium carbonate (extracting solution 3) is used.

Example 2

In this example, Br contained in the encapsulating resin was analyzed for the resin encapsulation semiconductor device having Au wires as shown in FIG. 4.

First, standard samples were prepared to make a calibration curve. The standard samples were prepared by adding a known concentration of Br to epoxy resin as the matrix resin. Using the standard samples, the calibration curve showing a relationship between the Br peak intensity obtained by an energy-dispersive fluorescent X-ray spectrometer and the Br concentration was made.

Next, a plurality of resin encapsulation semiconductor devices shown in FIG. 4 were aligned with each of upper and lower surfaces of the devices brought into a plane as shown in FIGS. 8A and 8B. The aligned devices were mounted on the sample holder with the upper or lower surfaces faced to the sample holder. A primary X-ray was applied to the upper or lower surfaces of the devices to detect a fluorescent X-ray, and spectrums shown in FIGS. 6A and 6B were obtained. FIG. 6A shows a fluorescent X-ray spectrum obtained by applying a primary X-ray to the upper surfaces of the devices, and FIG. 6B shows a fluorescent X-ray spectrum obtained by applying a primary X-ray to the lower surfaces of the devices. The intensity of Br—Kα line was 544.124 cps in FIG. 6A and 315.838 cps in FIG. 6B.

The spectrums were normalized with the scattered X-ray intensity, and Br content was determined using the calibration curve.

In addition, the above resin encapsulation semiconductor device was separately subjected to precision chemical analysis.

Table 1 shows the Br content obtained by the method of Example 2 and the precision chemical analysis.

TABLE 1

| Analyzed surfaces | Fluorescent X-ray analysis (ppm) | Precision chemical analysis (ppm) | Error (%) |
|---|---|---|---|
| Upper surfaces | 9000 | 7370 | 22 |
| Lower surfaces | 7880 | 7370 | 7 |

Since the resin encapsulation semiconductor device has Au wires on the upper surface side, when the fluorescent X-ray analysis is performed on the upper surfaces of the devices, Au peaks are detected. As shown in FIG. 6A, the peaks of the Br—Kα line and Au-Lβ line are close to each other in energy. Thus, when the Au peaks are detected, the apparent analytical value of Br is raised, which becomes a cause of a positive error. On the other hand, when the fluorescent X-ray analysis is performed on the lower surfaces of the devices, Au peaks are hardly detected (FIG. 6B). The error of the analytical value by the fluorescent X-ray analysis to that by the precision chemical analysis is 22% when the analysis is performed on the upper surfaces because of the influence of Au peaks. In contrast, the error is 7% because Au peaks are hardly detected when the analysis is performed on the lower surfaces, making it possible to perform very precise analysis.

As described above, when resin encapsulation semiconductor devices are aligned and Br contained in the devices is analyzed, application of the primary X-ray to the lower surfaces of the devices enables highly precise analysis. Further, inferior resin encapsulation semiconductor devices can be judged in high precision.

Example 3

Using the same resin encapsulation semiconductor devices as in Example 2, Sb contained in the encapsulating resin was analyzed by fluorescent X-ray analysis. Spectrums shown in FIGS. 7A and 7B were obtained. FIG. 7A shows a fluorescent X-ray spectrum obtained by applying a primary X-ray to the upper surfaces of the devices, and FIG. 7B shows a fluorescent X-ray spectrum obtained by applying a primary X-ray to the lower surfaces of the devices. The intensity of Sb—Kα line was 181.954 cps in FIG. 7A and 138.015 cps in FIG. 7B. Since Sb peaks do not influenced by Au peaks, it is preferable to apply the primary X-ray to larger amount of encapsulating resin. As shown in FIGS. 4, 8A and 8B, the resin encapsulation semiconductor device has a thicker encapsulating resin and has a smaller area ratio of lead frame on the upper surface side than the lower surface side. Therefore, when resin encapsulation semiconductor devices are aligned and Sb contained in the devices is analyzed, application of the primary X-ray to the upper surfaces of the devices enables highly precise analysis.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for controlling a hazardous element in an encapsulating resin of a resin encapsulation semiconductor device, comprising:
    subjecting the device to qualitative analysis with a fluorescent X-ray analyzer to judge whether the hazardous element is contained in the encapsulating resin;
    aligning a plurality of devices with each of upper and lower surfaces of the devices brought into a plane;
    setting the surfaces of the devices to cover a full X-ray irradiation plane and subjecting the devices to quantitative analysis with the fluorescent X-ray analyzer to obtain an analytical value of the hazardous element in the encapsulating resin for upper and lower surfaces of the devices; and
    judging whether the analytical value of the hazardous element which is less influenced by a coexistent element of the analytical values for the upper and lower surfaces of the devices exceeds a threshold value.

2. The method according to claim 1, wherein the qualitative analysis uses a calibration curve prepared for standard samples comprising an epoxy resin as a matrix resin.

3. The method according to claim 1, wherein the analytical value of the hazardous element is obtained through background correction by normalizing X-ray fluorescence intensity of the hazardous element with scattered X-ray intensity.

4. The method according to claim 1, wherein the hazardous element is selected from the group consisting of Br and Sb.

5. The method according to claim 1, wherein the coexistent element is at least one element selected from the group consisting of Au, Si, Cu, Fe, Ni, Sn, Bi, Pb, and Ag.

* * * * *

UNITED STATES PATENT AND TRADEMARK OFFICE
CERTIFICATE OF CORRECTION

PATENT NO. : 8,223,917 B2  Page 1 of 1
APPLICATION NO. : 12/575745
DATED : July 17, 2012
INVENTOR(S) : Oki et al.

It is certified that error appears in the above-identified patent and that said Letters Patent is hereby corrected as shown below:

Title Page, Item (75) Inventor is corrected to read:
-- Mitsuhiro Oki, Yokohama (JP);
Miyuki Takenaka, Yokohama (JP);
Tetsuya Tachibe, Yokohama (JP) --.

Signed and Sealed this
Twenty-third Day of February, 2016

Michelle K. Lee
*Director of the United States Patent and Trademark Office*

UNITED STATES PATENT AND TRADEMARK OFFICE
CERTIFICATE OF CORRECTION

PATENT NO. : 8,223,917 B2  
APPLICATION NO. : 12/575745  
DATED : July 17, 2012  
INVENTOR(S) : Mitsuhiro Oki et al.

It is certified that error appears in the above-identified patent and that said Letters Patent is hereby corrected as shown below:

"Title Page, Item (75) Inventor is corrected to read:
-- Mitsuhiro Oki, Yokohama (JP);
   Miyuki Takenaka, Yokohama (JP);
   Tetsuya Tachibe, Yokohama (JP) --."

(as corrected to read in the Certificate of Correction issued February 23, 2016) is deleted and patent is returned to its original state with the Inventors name in patent to read
--Mitsuhiro Oki, Yokohama (JP); Miyuki Takenaka, Yokohama (JP)--

Signed and Sealed this
Seventh Day of June, 2016

Michelle K. Lee
*Director of the United States Patent and Trademark Office*